United States Patent [19]
Matsuda et al.

[11] Patent Number: 6,103,488
[45] Date of Patent: Aug. 15, 2000

[54] METHOD OF FORMING UBIQUINONE-10

[75] Inventors: Hideyuki Matsuda; Makoto Kawamukai; Tsuyoshi Nakagawa; Katsunori Tanaka, all of Shimane-ken, Japan

[73] Assignee: Alpha Foods Co., Ltd., Shimane-ken, Japan

[21] Appl. No.: 09/009,895

[22] Filed: Jan. 21, 1998

[30] Foreign Application Priority Data

Aug. 27, 1997 [JP] Japan .................................. 9-244811

[51] Int. Cl.[7] ................ C12P 1/00; C12N 1/20; C07H 21/04
[52] U.S. Cl. .................. 435/41; 435/232; 435/252.33; 435/320.1; 536/23.2; 536/23.7
[58] Field of Search ................ 435/232, 252.33, 435/252.3, 320.1; 536/23.2, 23.7

[56] References Cited
PUBLICATIONS

Abstracts of Lectures of General Congress 1997 of Japan Society for Bioscience, Biotechnology, and Agrochemistry; Extra Edition, vol. 71, Mar. 1997.

K. Okada et al; Journal of Bacteriololgy; The ispB Gene Encoding Octaprenyl Diphosphate Synthase Is Essential for Growth of *Esherichia coli*; vol. 179, No. 9, pp. 3058–3060, May 1997.

K. Okada et al; Journal of Bacteriology; Cloning of the sdsA gene Encoding Solanesyl Diphosphate Synthase from *Rhodobacter capsulatus* and Its Functional Expression in *Escherichia coli* and *Saccharomyces cerevisiae*; vol. 179, No. 19, pp. 5992–5998; Oct. 1997.

*Primary Examiner*—Nashaat T. Nashed
*Attorney, Agent, or Firm*—Browdy and Neimark, P.L.L.C.

[57] ABSTRACT

The present invention relates to production of ubiquinone-10 in *E. coli* by isolating and sequencing a structural gene dds1 of decaprenyl diphosphate synthase derived from photosynthetic bacteria such as *Rhodobacter capsulatus.*, and expressing it in *E. coli*.

26 Claims, 8 Drawing Sheets

FIG. 2

```
                                                     S1 FOR DOWNSTREAM
                                              ████████████████████████████
         CTG GTA CAT GAC GTA GTC GAT GAA TCT                              484
         L   V   H   D   V   V   D   E   S                                 94
GCA AAT GCG ACA TGG AAT CAG ACT GCG                                       538
 A   N   A   T   W   N   Q   T   A                                       112
GCC CGG GCA TTT GAT CTG GTT GAT CTG                                       592
 A   R   A   F   D   L   V   D   L                                       130
TTC TCT ACA GGA ACC TGT GAG ATT GCT GAG                                   646
 F   S   T   G   T   C   E   I   A   E                                   148
CAG CAT CAG CCA GAT ACA GAA GAT ATT                                       700
 Q   H   Q   P   D   T   E   D   I                                       166
ACC TCA CGG TTG TTC GAA CTG GCG ACC GAA                                   754
 T   S   R   L   F   E   L   A   T   E                                   184
GAA TAC TGT GAA ┌CCT TTA CGT CGT TTT┐                                     808
 E   Y   C   E  │ P   L   R   R   F │                                    202
                └─────────────────────┘
                  S2 FOR UPSTREAM
GAT GAT
 D   D
  S1 FOR UPSTREAM

S2 FOR DOWNSTREAM
█████████████████████████
GGC
 G
GTA CTG GTG GGG GAT TTT CTG ATT
 V   L   V   G   D   F   L   I
GAC AAT ATG ATC CTG AAG GAC ATT
 D   N   M   I   L   K   D   I
GGT GAA GTA TTG CAG TTG CAG GCA
 G   E   V   L   Q   L   Q   A
TAT TTA CAG ATT CAC CTG GCA AAA
 Y   L   Q   I   H   L   A   K
GGC GCT GCA ATA CTG GCA GGC AAA
 G   A   A   I   L   A   G   K
┌GCC GGA┐ CAC TTT
│ A   G │ H   F
└───────┘
          G   N   A   F   Q   I
           S1 FOR UPSTREAM
```

PRIMERS FOR UPSTREAM     :S1 ████    :5'- AAT AAT CTG AAA AGC ATT GCC
AMPLIFICATION            :S2 ▭      :5'- TCC GGC AAA ACG ACG TAA AGG

PRIMERS FOR DOWN-        :S1 ████    :5'- CAT GAT GAT GTG GTA GAT GAG
STREAM AMPLIFICATION     :S2 ████    :5'- TTA CGT CGT TTT GGC AGA CCA ACA

```
AAG AAT ATA CTC AAA GGC AGC GGA CCC TAA ACT AAA GGC TCC CGT CTG GTT TAA       54

GCC CTA GAA TTT TGG CTA CCT TCC TGG CTG CTT TAG GAT ACA ATA GCT TTA ATT      108

TTT TAA GTA TCA GAT ATC TAA AAG CTG GTT ACG GTG TTT AGA CGT CTC ACT GTT      162

TAA CTG TGC ATC CGA TTA CTT TCG CAA GAG GTT CTT TTT CAT ATG GCC ATC GAT      216
                                                          M   A   I   D        4
TTC AAG CAA GAT ATT CTC GCT CCT GTT GCT CAA GAT TTG CAG CGA TGG ACC AGT      270
 F   K   Q   D   I   L   A   P   V   A   Q   D   L   Q   R   W   T   S       22
TTA TTA ATG AAG GAA TCA GCT CCA AAG GTC GCA CTG GTC ATG TCA GTC AGC AAG      324
 L   L   M   K   E   S   A   P   K   V   A   L   V   M   S   V   S   K       40
CAT GTC GTT GAA GCA GGT GGA AAG CGC ATG CGT CCG ATT ATG TGC TTG CTG GCC      378
 H   V   V   E   A   G   G   K   R   M   R   P   I   M   C   L   L   A       58
GCT TAT GCC TGT GGT GAA ACC AAT TTA AAG CAT GCA CAG AAG CTG GCG GCC ATT      432
 A   Y   A   C   G   E   T   N   L   K   H   A   Q   K   L   A   A   I       76
ATT GAA ATG CTG CAT ACG GCG ACT CTG GTA CAT GAT GAT GTG GTA GAT GAG TCT      486
 I   E   M   L   H   T   A   T   L   V   H   D   D   V   V   D   E   S       94
GGC TTA CGC CGT GGC AGA CCA ACA GCA AAT GCG ACA TGG AAT AAC CAG ACT GCG      540
 G   L   R   R   G   R   P   T   A   N   A   T   W   N   N   Q   T   A      112
GTA CTG GTG GGG GAT TTT CTG ATT GCC CGG GCA TTT GAT CTG CTG GTT GAT CTG      594
 V   L   V   G   D   F   L   I   A   R   A   F   D   L   L   V   D   L      130
GAC AAT ATG ATC CTG TTA AAG GAC TTC TCT ACA GGA ACC TGT GAG ATT GCT GAG      648
 D   N   M   I   L   L   K   D   F   S   T   G   T   C   E   I   A   E      148
GGT GAA GTA TTG CAG TTG CAG GCA CAG CAT CAG CCA GAT ACA ACA GAA GAT ATT      702
 G   E   V   L   Q   L   Q   A   Q   H   Q   P   D   T   T   E   D   I      166
TAT TTA CAG ATT ATT CAC GGT AAA ACC TCA CGG TTG TTC GAA CTG GCG ACC GAA      756
 Y   L   Q   I   I   H   G   K   T   S   R   L   F   E   L   A   T   E      184
GGC GCT GCA ATA CTG GCA GGC AAA CCT GAA TAC TGT GAA CCT TTA CGT CGT TTT      810
 G   A   A   I   L   A   G   K   P   E   Y   C   E   P   L   R   R   F      202
GCC GGA CAC TTT GGC AAT GCT TTT CAG ATT ATT GAT GAT ATT CTG GAT TAC ACT      864
 A   G   H   F   G   N   A   F   Q   I   I   D   D   I   L   D   Y   T      220
TCA GAT GCT GAT ACG CTC GGC AAA AAT ATT GGC GAT GAC TTG ATG GAA GGC AAA      918
 S   D   A   D   T   L   G   K   N   I   G   D   D   L   M   E   G   K      238
CCC ACC CTG CCG CTG ATT GCA GCA ATG CAA AAT ACT CAA GGT GAA CAG CGC GAC      972
 P   T   L   P   L   I   A   A   M   Q   N   T   Q   G   E   Q   R   D      256
CTG ATC CGT CGC AGC ATT GCC ACT GGC GGT ACT TCA CAG CTT GAA CAA GTT ATT     1026
 L   I   R   R   S   I   A   T   G   G   T   S   Q   L   E   Q   V   I      274
GCG ATT GTA CAA AAT TCG GGA GCG CTG AAT TAT TGC CAT AAG CGT GCT ACT GAA     1080
 A   I   V   Q   N   S   G   A   L   N   Y   C   H   K   R   A   T   E      292
GAA ACC GAG CGA GCA TTA CAG GCA CTA GAA ATA TTA CCT GAG AGT ACT TAC CGG     1134
 E   T   E   R   A   L   Q   A   L   E   I   L   P   E   S   T   Y   R      310
CAG GCG CTG GTT AAC TTG ACC CGC TTA GCT TTA GAC CGA ATC CAA TAA TAT TAT     1188
 Q   A   L   V   N   L   T   R   L   A   L   D   R   I   Q   *              325
TAA AAA TTT TAT GCA TTT AAA CTT TCA AGA TCT TTT TCT CAG AAT GCA CCA GCA     1242

GCT TGA GCA ACC TCA AGC TGT ATT AGA TGA AAA TAT TCT TAT TGA GCT GGT TAA     1296

CCG CCT ACG CCC CGC TGA TAC CAA AAA TAC CGA AGA AAT TGA AAG AAA ATT TCA     1346

GGC ATT TAT CCA GTC GCT TTT AAT TAC ACC GGC TGC TGC CTG TTA CAT TTC         1401
```

STRAIN FROM WHICH PLASMID pKA3 IS NOT DELETED

STRAIN FROM WHICH PLASMID pKA3 IS DELETED

FIG. 10

METHOD OF FORMING UBIQUINONE-10

TECHNICAL FIELD TO WHICH THE INVENTION BELONGS

The present invention relates to formation of ubiquinone, particularly ubiquinone-10. The present invention relates in particular to a novel system for forming ubiquinone-10 by isolating and expressing a gene coding for decaprenyl diphosphate synthase (also referred to DDS) derived from photosynthetic bacteria.

PRIOR ART

Isoprenoid is a natural organic compound of which the fundamental unit is C5 isopentenyl diphosphate (IPP) and occurs widely in the nature. Examples are pigment carotinoid, natural rubber, and isoprenoid quinones acting in the respiratory chain electron transport system. The isoprenoid quinones include a few members such as ubiquinone (UQ), menaquinone and plastoquinone, which are distinguished depending on the difference in the quinone skeleton, and each member has a large number of homologues depending on a difference in the length of its isoprenoid side chain.

Ubiquinone is a compound having isoprenoid added to the quinone skeleton, and it is a biological component also called coenzyme (CoQ) having the structure of 2,3-dimethoxy-5-methyl-6-polyprenyl-1,4-benzoquinone playing an important role.

Ubiquinone occurs as a component in animal and plant tissues and as a microbial component in microorganisms and it is a vitamin-like component also known as anti-oxidant and plays a biologically and biochemically important role as an essential component in the electron transport system. Its analogues ranging mainly from ubiquinone-1 to ubiquione-12 depending on the number of isoprenoid units in the side chain occur in nature.

Ubiquinone is studied for pharmacological and clinical effects as well and is considered to have an effect on congestive cardiac insufficiency, muscular dystrophy, anemia etc. Accordingly, it is a substance of high values as a drug for treatment of cardiac diseases and as other pharmaceutical preparations. However, only ubiquione-10 was confirmed to have effect as a pharmaceutical preparation. At present, ubiquinone-10 has been extracted and purified from tobacco leaves, yeast or other microorganisms, but its details are not revealed. In addition, its production does not catch up with its demand, so it is required to develop a further efficient process as a substitute for the conventional process.

Isoprenoid, which forms a side chain of this ubiquinone, is a natural organic compound with the fundamental unit of 5C isopentenyl diphosphate (IPP) and occurs widely in nature. Besides its role as a side chain of ubiquinone, its features as carotinoid, natural rubber and prenylated protein are also known.

In in vivo biosynthesis, new IPPs are linked to fundamental IPP and FPP (farnesyl diphosphate) thus elongating its chain to form long-chain isoprenoid. An enzyme catalyzing synthesis of isoprenoid in this manner is called prenyl transferase.

The presence of many kinds of prenyl transferase has been confirmed in mainly bacteria. The presence of three enzymes FPS, OPS and UPS has been confirmed in *E. coli*, and the structural gene ispA of FPS and the structural gene ispB of octaprenyl diphosphate synthase (OPS) have been isolated as genes.

By the action of this prenyl transferase, octaprenyl diphosphate with an 8-carbon side chain is synthesized in *E. coli*, and hexaprenyl diphosphate with a 6-carbon side chain is synthesized in budded yeast. Meanwhile, these isoprenoids are added to a benzoquinone skeleton derived from PHB (p-hydroxybenzoate) by an ubiA product in *E. coli* and a COQ2 product in yeast to complete ubiquinone-8 and ubiquinone-6, respectively. Accordingly, the point catalyzed by the ispB product, ubiA product, etc., is considered important for synthesis of ubiquinone.

Ubiquinone-10 draws attention as a physiologically active substance with high pharmaceutically activity as described above, and the present inventors have the new point of view that use of a gene of decaprenyl diphosphate synthase for synthesis of side chains, the ubiA product, and the yeast COQ2 product, can leads to efficient production of ubiquinone-10, and they focused their attention on the necessity for cloning of the decaprenyl diphosphate synthase gene.

PROBLEM TO BE SOLVED BY THE INVENTION

Under the technical circumstances described above, the present invention was made for the purpose of developing the techniques of producing UQ-10 in microorganisms by use of a gene involved in synthesis of decaprenoid as a side chain of UQ-10.

MEANS TO SOLVE THE PROBLEM

The present invention was made to achieve the above object, and as a result of extensive examination, the present inventors atempted to produce UQ-10 by isolating a gene necessary for synthesis of UQ-10, that is, a gene for decaprenyl diphosphate synthase necessary for synthesizing its side chain, from an organism producing physiologically active UQ-10 and then expressing the gene in *E. coli*.

To solve this novel technical problem, the present inventors synthesized a mixture of primers designed on the basis of amino acid sequences (amino acid sequences of domains 2 and 6) located in common in various polyprenyl diphosphate synthases (PDSs), and these primers were used to conduct PCR where the genomic DNA from photosynthetic bacterium *Rhodobacter capsulatus* biosynthesizing UQ-10 was used as the template. Sequencing of the amplification fragment obtained by the PCR suggested that it was a DNA fragment containing the target gene, so genome walking by PCR using cassette and cassette primer at its upstream and downstream sides was conducted to give a gene fragment considered to contain its full-length sequence. The nucleotide sequence of this gene fragment was then determined.

As a result, the presence of an ORF consisting of 978 bp (325 amino acids) was confirmed, and as a result of further homology examination, the amino acids deduced from this nucleotide sequence showed high homology with the amino acids of Dds1 (decaprenyl diphosphate synthase) from acetic acid bacterium *Gluconobacter suboxydans* and IspB (octaprenyl diphosphate synthase) from *E. coli*, respectively.

From the foregoing, the gene cloned in this manner was identified as a gene coding for decaprenyl diphosphate synthase, and it was designated dds1 gene. This gene was cloned in an *E. coli* expression vector. As a result of expression using a promoter for *E. coli* lacZ gene, the formation of UQ-9 and UQ-10 was confirmed in addition to UQ-8 originally possessed by the host, and Dds activity was also present.

In addition, *E. coli* from which an octaprenyl diphosphate synthase gene (ispB gene) necessary for synthesis of UQ-8 had been deleted was prepared, and separately, the dds1 gene was cloned in an *E. coli* expression vector in the same manner as described above, and it was confirmed that UQ-10 could be produced as the major product by expressing the gene in the the ispB-destroyed strain prepared above.

As a result, the present inventors succeeded for the first time in production of UQ-10 where in the former case, UQ-10 could be produced along with UQ-8 and UQ9, while in the latter case, UQ-10 can be produced mainly in the ispB destroyed strain to enable efficient production of high-purity UQ-10, and on the basis of these findings, the present inventors arrived at the present invention.

BRIEF DESCRIPTION OF THE DRAWINGS

FIG. 2 shows the design of specific primers S1 and S2 for PCR. The nucleotide and amino acid sequence shown in the upper part of FIG. 2 correspond to nucleotides 454–847 of SEQ ID NO:1 and residues 85–215 of SEQ ID NO:2, respectively. Primer S1 for upstream amplification is SEQ ID NO:7. Primer S2 for upstream amplification is SEQ ID NO:8. Primer S1 for downstream amplification is nucleotides 460–481 of SEQ ID NO:1. Primer S2 for downstream amplification is nucleotides 488–509 of SEQ ID NO:1.

EMBODIMENT FOR CARRYING OUT THE INVENTION (1) Cloning of dds1 Gene Coding for Decaprenyl Diphosphate Synthase (DDS) from *R. capsulatus* a) Preparation of primers and PCR

Sense primer A and antisense primer B were prepared on the basis of the amino acid sequences of domains II and VI particularly conserved among highly conserved 7 regions located in an enzyme (prenyl diphosphate synthase, PDS) synthesizing isoprenoid.
Primer A:
5'-YTNYTNCAYGAYGAYGT-3' (SEQ ID NO:3)
Primer B:
5'-RTCNTCNAGYTGRTT-3' (SEQ ID NO:3)
where Y is T or C; N is A, C, T or G; and R is A or G.

Primers A and B were used to conduct PCR where the genomic DNA of *R. capsulatus* was used as a template. About 0.5 μg of the genome was thermally denatured at 94° C. for 5 minutes. The reaction involved 25 cycles of PCR, each cycle consisting of thermal denaturation at 94° C. for 30 seconds, annealing to the primers at 55° C. for 2 minutes and elongation reaction at 72° C. for 2 minutes. Then, a part of the reaction solution was subjected to agarose gel electrophoresis, and an amplification product of about 400 bp or thereabout could be confirmed.

b) Cloning of the PCR amplification fragment

Figure 1:
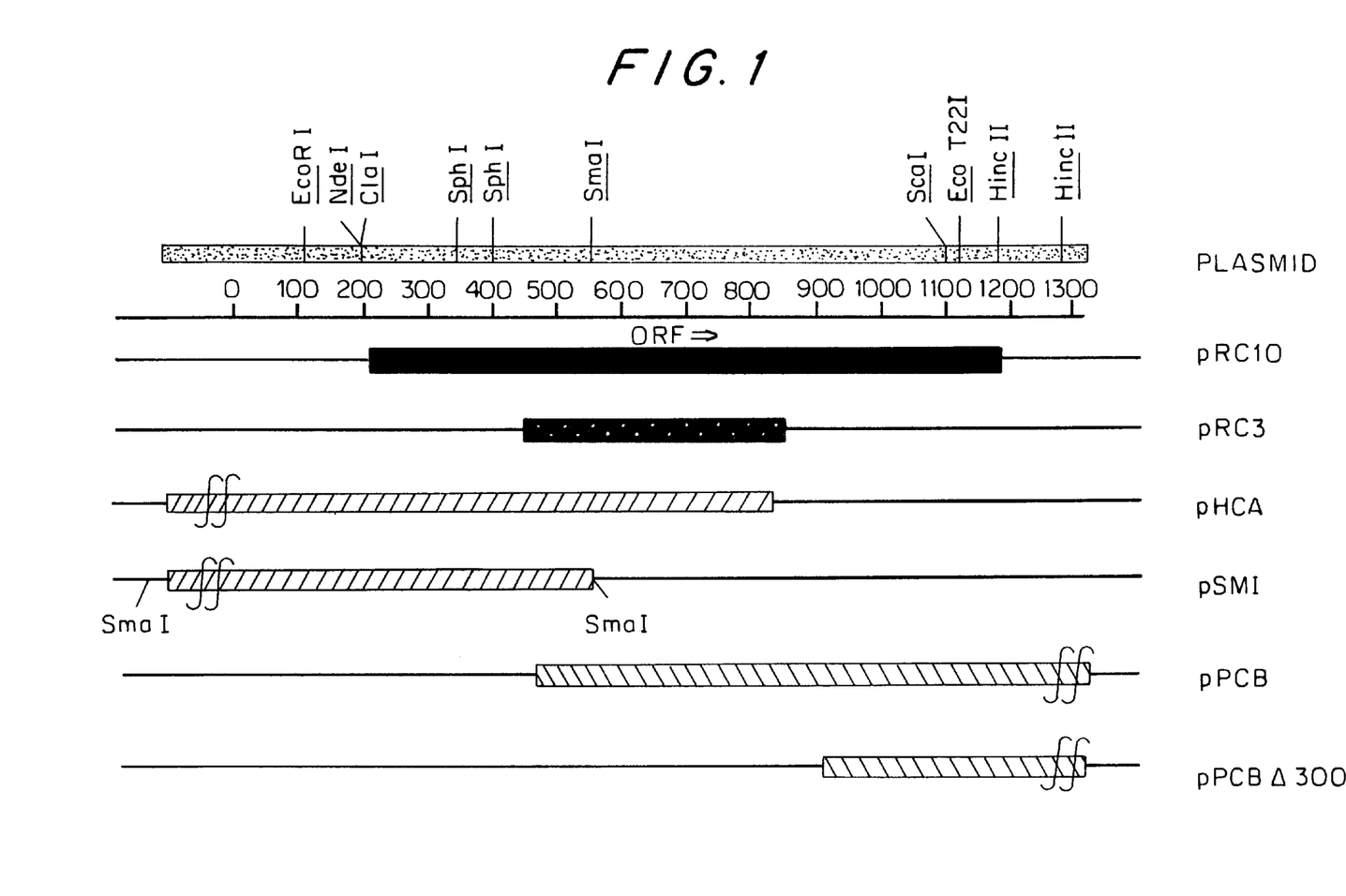
FIG. 1 shows a restriction enzyme map of the constructed plasmid.

Because a restriction enzyme BamHI recognition site had been added to the 5'-terminal of each of primers A and B, this site was utilized for cloning. Vector pUC18 and the amplification fragment were digested with BamHI, and the vector was subjected to treatment with BAP. DNA ligation Kit Ver. 1 (Takara Shuzo Co., Ltd.) was used for ligation, and a part of the ligation product was introduced into *E. coli* DH10B by the Hanahan method, and the plasmid was extracted from a clone considered to have the target gene and then confirmed by restriction enzyme reaction. The constructed plasmid was designated pRC3 (FIG. 1).

c) Sequencing of the PCR amplification fragment

Sequencing was carried out in ABI PRISMTM 377 DNA Sequencer. pRC3 as a template was sequenced starting at both ends by use of universal and reverse primers. When its coding amino acid sequence was examined for homology with other prenyl diphosphate synthase, it was found to have high homology with a long-chain synthases, that is, octaprenyl diphosphate synthase (48.8% homology) encoded by ispB in *E. coli* and polyprenyl diphosphate synthase encoded by ispB in *H. Influenzae* (47.7% homology). The photosynthetic bacterium *R. capsulatus* biosyntheses UQ-10 and is thus considered to have decaprenyl diphosphate synthase activity, so the about 400 bp fragment thus cloned was estimated to be a part of the gene dds1 coding for decaprenyl diphosphate synthase.

Figure 2:
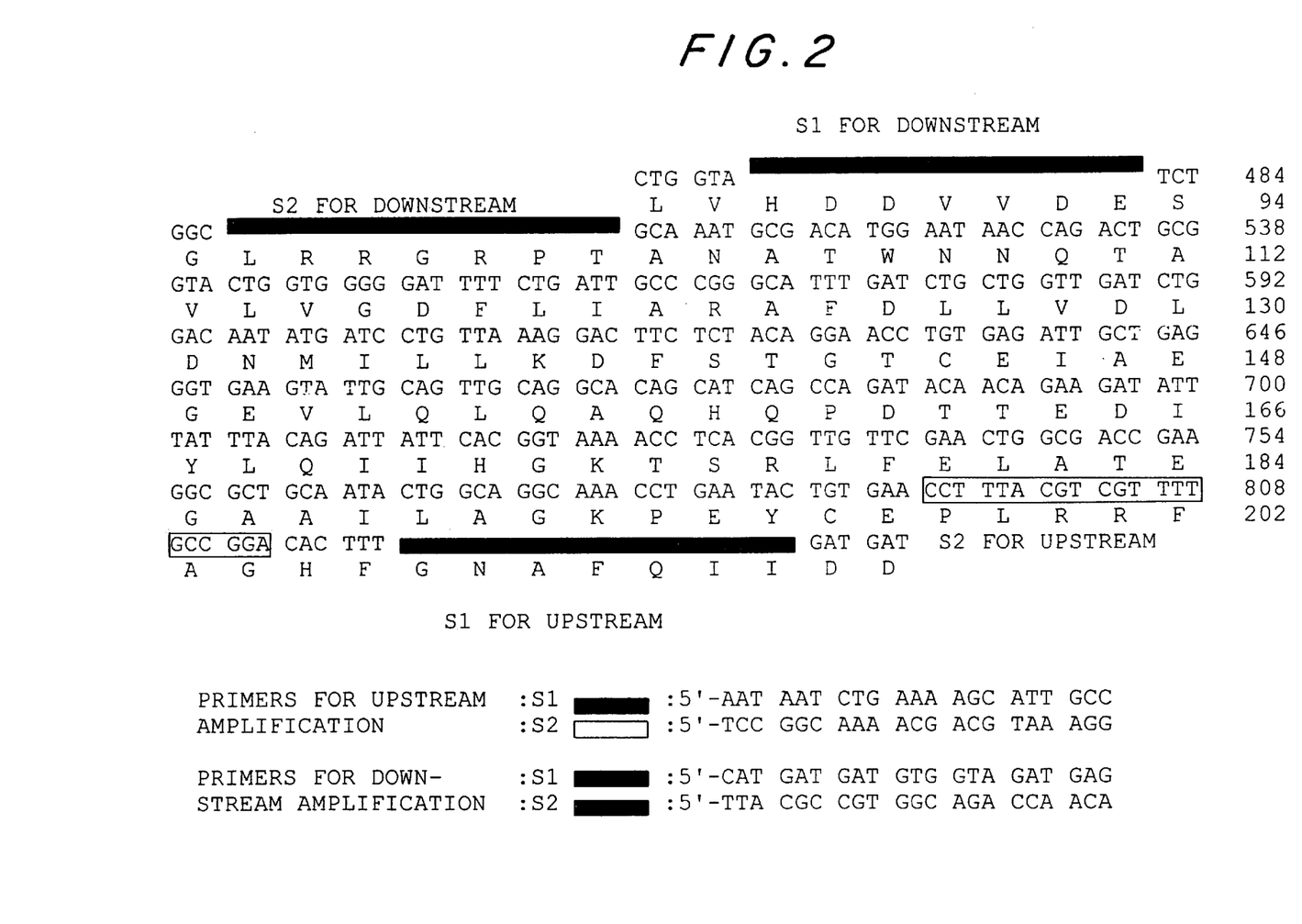
Figure 3:
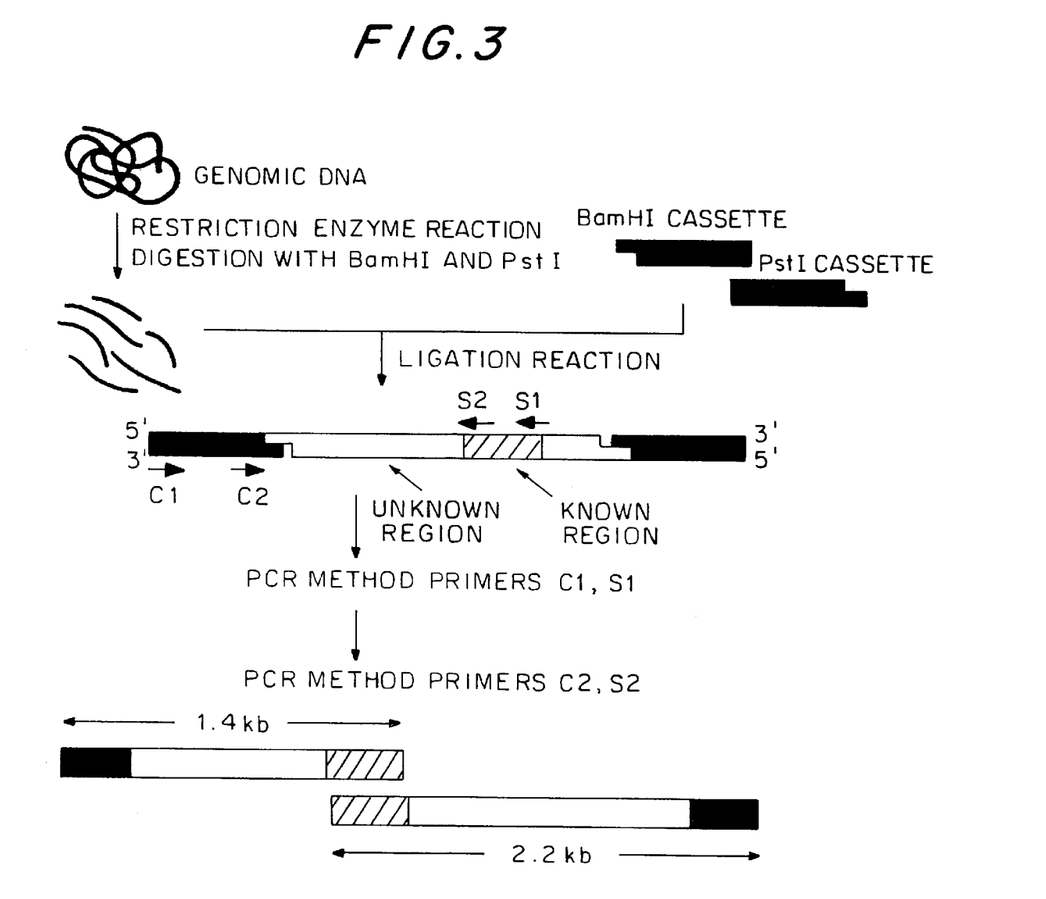
FIG. 3 shows genome walking by PCR by use of cassettes and cassette primers.

(2) Cloning of the Full-length dds1 Gene by Use of Cassettes and Cassette Primers a) PCR using cassettes and cassette primers Screening after construction of the plasmid library did not result in cloning of the full length dds1 gene, but the presence of the dds1 gene was confirmed in PCR to be present in the constructed library. Therefore, the present inventors thought that if the probe (400 bp or less) used in screening is larger, false-positiveness may be reduced, so the strategy of elongating a probe or cloning its full length by genome walking in PCR using Takara's cassettes and cassette primers. As shown in FIG. 2, primers S1 and S2, which were complementary to the sequence of a part (about 400 bp) already cloned of the dds1 gene, were synthesized as primers for amplifying its upstream and downstream regions. Because commercially available cassettes are EcoRI, HindIII, PstI, SalI, XbaI and Sau3AI Cassettes, the corresponding restriction enzymes were used to digest genomic DNA from *R. capsulatus*, and the resulting fragment was ligated to each cassette by use of Ligation high (Toyobo). A part of the ligation product was subjected, as the template, to first PCR using cassette primer C1 1 and primer S1 complementary to the known region. Then, 1 μl of the first PCR reaction solution was used to carry out second PCR, and the product was subjected to electrophoresis. As a result, about downstream 1.4 kb and upstream 2.2 kb specific amplification products were observed which resulted from amplification using the ligated PstI cassette and the ligated HindIII cassette respectively. However, PCR using other cassettes resulted in a plurality of unspecific amplification fragments, so their cloning was difficult (FIG. 3).

b) Cloning of the upstream and downstream amplification fragments

First, the upstream amplification fragment, 1.4 kb, and the downstream amplification fragment, 2.2 kb, were confirmed to be parts of the dds1 gene by Southern hybridization, and its cloning was then carried out. "A" is added to the terminal of the PCR amplification fragment because of the character of LA Taq DNA polymerase used in PCR. Hence, the amplification fragment was ligated into vector pT7 Blue T-Vector (Novagen) with one nucleotide (T) protruded at the 3'-side, and a part of the reaction solution was introduced into E. coli JM109 by electroporation. Plasmids were extracted to obtain plasmids pHCA and pPCB having the target upstream amplification fragment 1.4 kb and downstream amplification fragment 2.2 kb inserted into them respectively (FIG. 1).

c) Determination of the nucleotide sequences
(Sequencing of the upstream region)

Plasmid pHCA having the amplification fragment, about 1.4 kb, inserted therein was subjected to sequencing reaction using universal primer and reverse primer and then it was sequenced by ABI PRISMT M377 DNA Sequencer. However, the size of the insert DNA was too large to determine the whole region, so its subcloning was conducted. As shown in FIG. 1, it was digested at the SmaI site in the vector and SamI site in the insert DNA and then the resulting fragment was cloned into the EcoRV site of pUC18 to construct plasmid pSMI. It was sequenced starting at both ends whereby the nucleotide sequence of the upstream amplification fragment, 1.4 kb, was determined.

(Sequencing of the downstream region)

Figure 4:
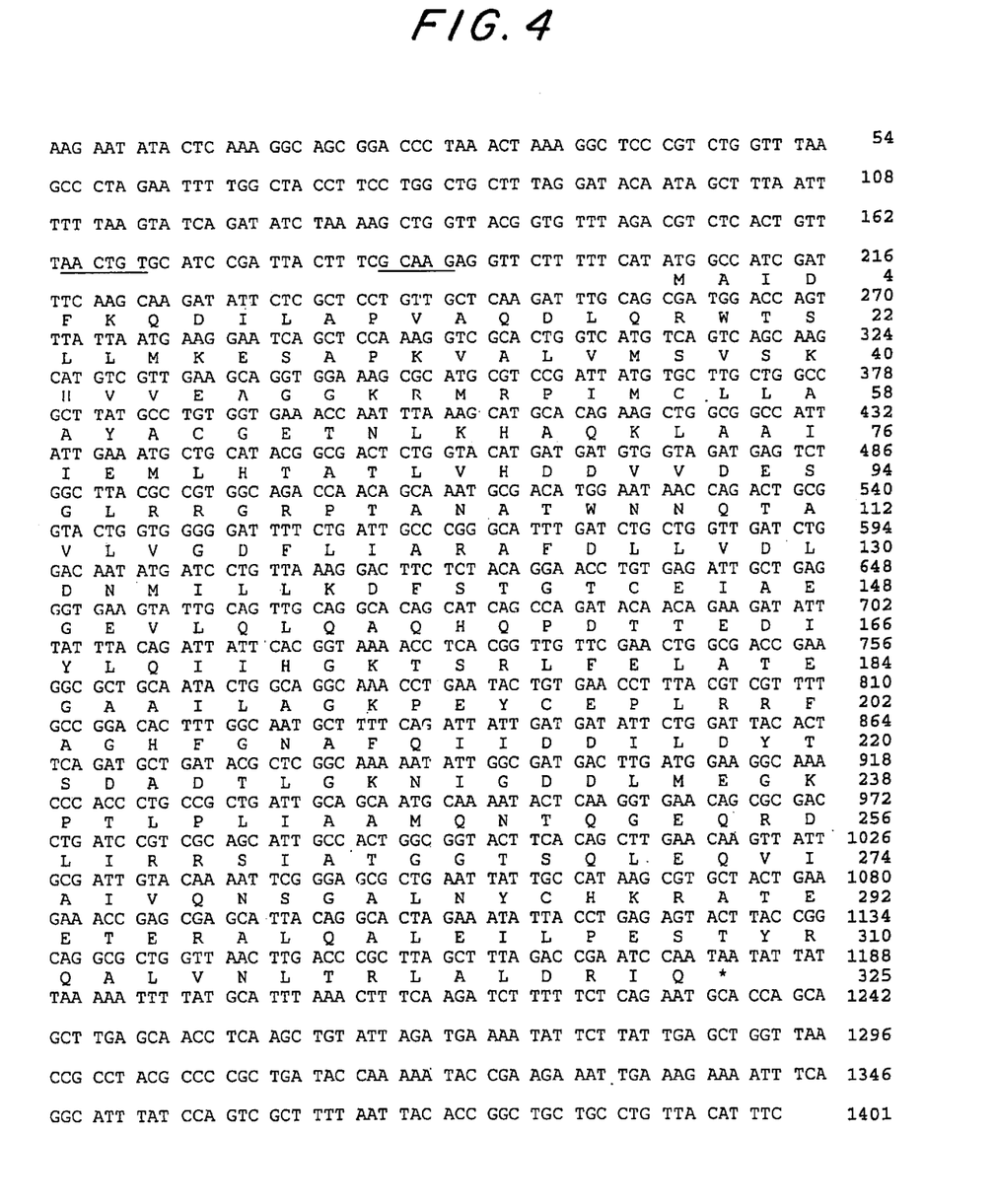
FIG. 4 shows a nucleotide sequence (SEQ ID NO:1) containing a gene (dds1) coding for Dds1 derived from *R. capsulatus*, and the amino acid sequence (SEQ ID NO:2) deduced from it. The termination codon is shown by the asterisk.

Plasmid pPCB having the downstream amplification fragment about 2.2 kb inserted therein was also sequenced using the universal primer and reverse primer in the same manner as for pHCA, and as a result, the universal primer side was found to be located at the N-terminal. To sequence the region whose nucleotide sequence could not be determined by this sequencing step, a deletion plasmid was constructed as follows: After the absence of KpnI and BamHI sites in the insert DNA was confirmed, pPCB was completely digested with KpnI and BamHI and then with Exonuclease III and Mung bean nuclease, to give plasmid pPCB Δ300 from which about 400 bp of the upstream region had been deleted. After ligation, the product was introduced into DH10B, and the target gene was isolated and sequenced. As a result, the presence of an ORF consisting of 978 kb (325 amino acids) was confirmed. Its nucleotide sequence and the amino acid sequence deduced from it were shown in FIG. 4.

(d) Examination of Homology

The amino acid sequence deduced from the nucleotide sequence of the ORF (open reading frame) i.e. the region whose genetic information is transcribed into mRNA and then translated into a protein has high homology with the amino acid sequences of other prenyl diphosphate synthases, that is, 43.6% homology with IspB from E. coli and 41.6% homology with Dds1 from acetic bacterium Gluconobacter suboxydans.

From this, the presently cloned gene is considered to be a structural gene of polyprenyl diphosphate synthase. The photosynthetic bacterium R. capsulatus biosyntheses UQ-10 and thus this gene was expected to code for a protein having decaprenyl diphosphate synthase activity, so this gene was designated gene dds1 coding for decaprenyl diphosphate synthase. The nucleotide sequence thereof, along with the amino acid sequence of DDS, were shown in SEQ ID NOs:1 (corresponding to nucleotides 205 to 1188) and 2, respectively.

Figure 5:
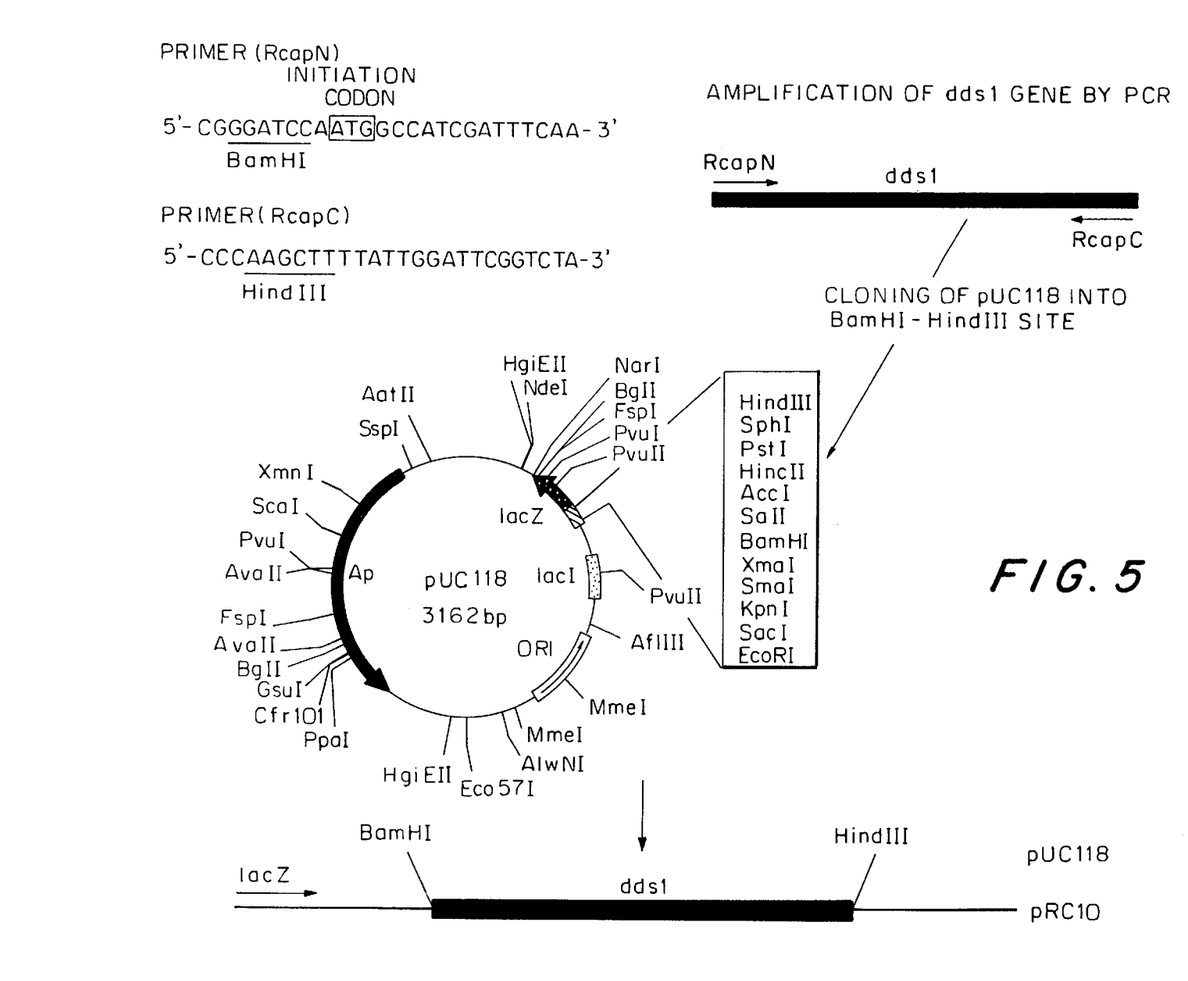
FIG. 5 shows construction of plasmid pRC10 for expression of dds1 gene Primer RcapN as shown is SEQ ID NO:5. Primer RcapC as shown is SEQ ID NO:6.

(3) Expression of the dds1 Gene in E. coli a) Construction of a plasmid for expression of the dds1 gene As shown in FIG. 5, PCR was carried out using primers RcapN and RcapC (to which restriction enzyme BamHI and HindIII sites had been added) capable of amplifying the ORF in the dds1 gene. Then, the amplification fragment was cloned into the BamHI-HindIII site in pUC118 to result in constructing plasmid pRC10 in which said fragment was inserted so as to be adjusted to the translational frame of lacZ gene.

b) Expression in E. coli (1)

Figure 6:
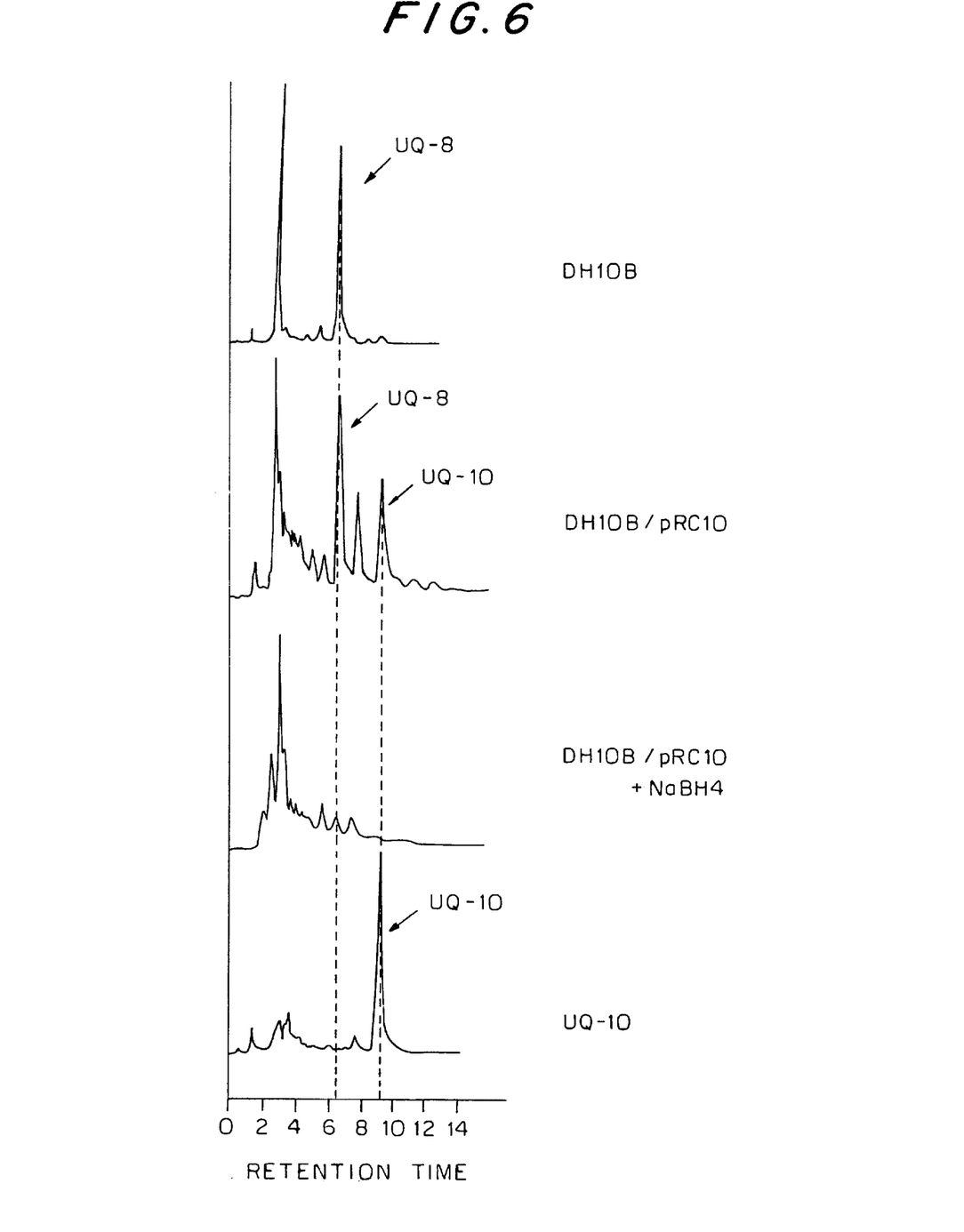
FIG. 6 shows a HPLC chromatogram of UQ extracted from a culture of *E. coli* DH10B/pRC10.

Plasmid pRC10 thus constructed was introduced into E. coli DH10B and cultured where IPTG (isopropyl-4-thio-β-D-galactoside) was added for induction at a concentration of 2 mM to the microorganism just before logarithmic growth phase. UQ was extracted from the E. coli, then developed by TLC and analyzed by HPLC, and a peak of UQ-10 was thus confirmed in addition to a peak of originally biosynthesized UQ-8 (FIG. 6). Because the peak of UQ-10 disappeared upon addition of the reducing agent $NaBH_4$, it was confirmed that the E. coli biosynthesised UQ-10.

As is evident from the foregoing, E. coli DH10B (Escherichia coli DH10B/pRC10), that is, a microorganism transformed with dds1 derived from R. capsulatus was confirmed to express dds1 and to produce UQ-10. This transformant was designated E. coli DH10B/pRC10 and deposited as FERM BP-6061 on Aug. 15, 1997 under the Budapest Treaty with the National Institute of Bioscience and Human-Technology, Agency of Industrial Science and Technology, Japan.

UQ extraction, TLC development, and HPLC analysis were carried out respectively as follows:

(UQ extraction)

50 ml culture (yeast cells) and 20 ml culture (E. coli) were centrifuged and 3 ml of acetone/methanol (7:2) was added to the pellet which was then sonicated for 30 seconds and placed in ice-cold water for 30 seconds. The above step was repeated 6 times. After centrifugation, the supernatant was dried under vacuum. 400 μl of chloroform/methanol (1:1) and an equal volume of 0.7% NaCl were added to the pellet and then stirred. After centrifugation, the lower layer was extracted, dried, and suspended in 100 μl of chloroform/methanol (2:1).

(TLC development)

The sample was spotted onto a TLC plate. It was developed with benzene/acetone (93:7) for about 1 hour, and UQ was confirmed by irradiation of the plate with UV ray. A part considered to contain UQ was scratched. 400 μl Chloroform/methanol (1:1) was added to it and stirred, and after centrifugation, the supernatant was dried under vacuum. It was suspended in 100 μl of 100% ethanol, and 20 μl of the resulting solution was used as analysis sample.

(HPLC analysis)

Analysis was carried out under the following conditions.

Column: Shim-pack CLC-ODS.

Eluent: 100% ethanol.

Flow rate: 1.0 ml/min.

Wavelength: 275 nm.

An example of formation of UQ-10 accompanied by UQ-8 by use of E. coli DH10B (E. coli DH10B/pRC10) (FERM BP-6061) transformed with plasmid pRC10 has been described, and another example is hereinafter described.

c) Expression in *E. coli* (2)

Figure 7:
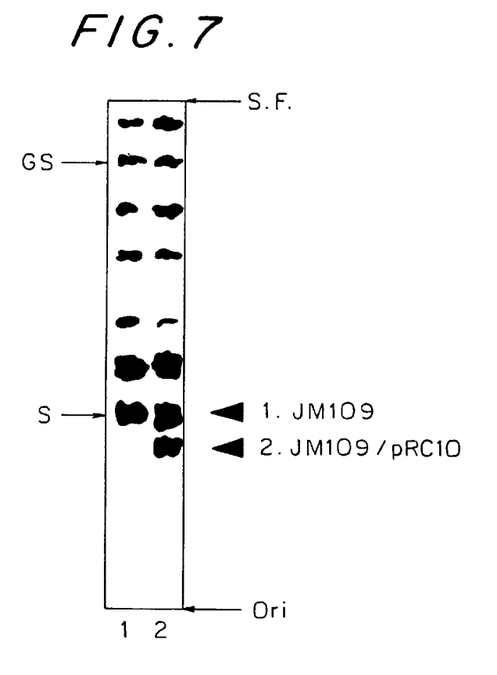
FIG. 7 shows a thin layer chromatogram of a product of *E. coli* JM109/pRC10.

*E. coli* JM109 (*Escherichia coli* JM109/pRC10) carrying pRC10, that is, a microorganism transformed in the same manner as above with dds1 derived from *R. capsulatus,* was cultured, and measurement of the activity of the dds1 gene product and identification of the product were carried out as follows:

$^{14}$C-labelled IPP (isopentenyl diphosphate: Amersham Life Science Co., Ltd.) and FPP (farnesyl diphosphate) were used as substrate, and a crude enzyme (0.05 mg protein) from *E. coli* where the gene was expressed was allowed to react with the substrate at 30° C. for 2 hours, and then polyprenyl diphosphate extracted with butanol was hydrolyzed and developed in the form of polyprenol by TLC. As a result, as shown in FIG. 7, decaprenol was detected in JM109 carrying pRC10 (lane 2). From the results, it was made evident that the dds1 gene obtained by the present inventors is a gene involved in synthesis of side chain decaprenyl diphosphate necessary for synthesis of UQ-10, and it was proved that formation of UQ-10 is made feasible by expression of the dds1 gene in *E. coli.*

As is evident from the drawings, lane 1 is JM109 as the control, where octaprenol is detected. On the other hand, in lane 2 (gene expression lane), solanesol and decaprenol are confirmed to be formed in addition to octaprenol, and from these results it was made evident that dds1 is a structural gene for solanesyl, decaprenyl diphosphate synthase.

Figure 8:
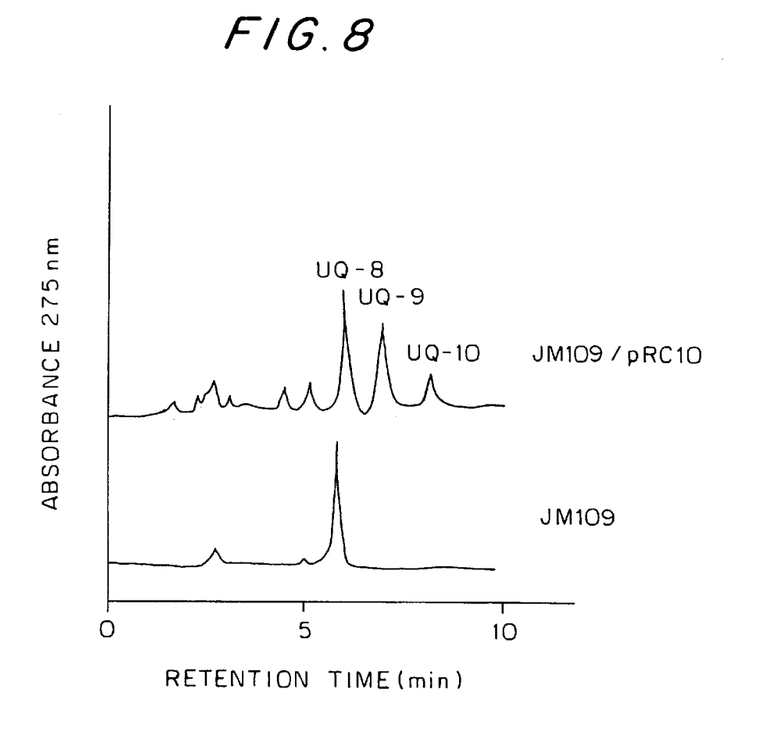
FIG. 8 shows a HPLC chromatogram of UQ extracted from a culture of *E. coli* JM109/pRC10.

Then, UQ was extracted from JM109 expressing dds1 and analyzed by HPLC, and peaks of UQ-9 and UQ-10 were confirmed in addition to a peak of originally biosynthesized UQ-8 (FIG. 8). On the other hand, JM109 as the control formed UQ-8 only, and from these results, the production of UQ-10 by *E. coli* JM109 (*Escherichia coli* JM109/pRC10) transformed with plasmid pRC10 was confirmed. In other words, dds1 is the structural gene of DDS and further its expression in the heterologous microorganism was confirmed.

(4) Test of Complementation with the Mutation in *E. coli* ispB-Deficient Strain KO 229 (ΔispB::CAT) by Dds1

Because *E. coli* KO229 is a strain in which ispB gene coding for octaprenyl diphosphate synthase in the genome has been destroyed by insertion of a gene coding for CAT (chloramphenicol acetyl transferase), it cannot biosynthesize UQ-8, and it cannot grow as such, so the mutation is complemented by introducing plasmid pKA3 carrying the ispB gene.

Generally, a plasmid not necessary for growth will not be segregated into daughter cells at the time of cell division so that the plasmid is deleted from it. However, because plasmid pKA3 (having spectinomycin resistant gene) possessed by KO229 complements a mutation and is thus essential for growth, pKA3 cannot be deleted even by several sub-cultures in a non-selective medium not containing spectinomycin. Hence, a plasmid deletion experiment was carried out considering that if the function of IspB in *E. coli* can be replaced in vivo by that of Dds1 protein, pKA3 having the ispB gene inserted into it can be deleted.

Figure 9:
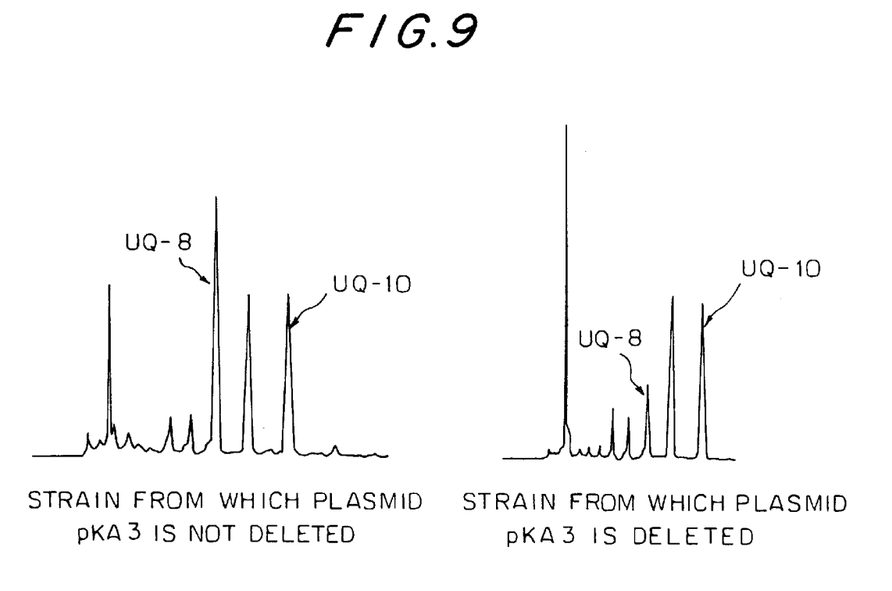
FIG. 9 shows a HPLC chromatogram of UQ from the pKA3-deficient strain.

That is, after pRC10 was introduced into KO229, the microorganism was subjected to several sub-cultures in a non-selective medium (Cm+Amp). Colonies were formed in a non-selective plate not containing spectinomycin and replicated in a non-selective plate and a selective plate (Cm+Spc), and some strains showing sensitivity to spectinomycin as the selective marker of pKA3, that is, strains considered to delete the plasmid, could be obtained. UQ was extracted from the strains showing sensitivity to spectinomycin and analyzed by HPLC, and as a result, peaks of UQ-9 and UQ-10 having isoprenoid chain with a length considered to be supplied by Dds1 protein were observed as shown in FIG. 9. This indicates that plasmid pKA3 could be successfully deleted by complementing the mutation with Dds1 protein in place of IspB protein.

Figure 10:
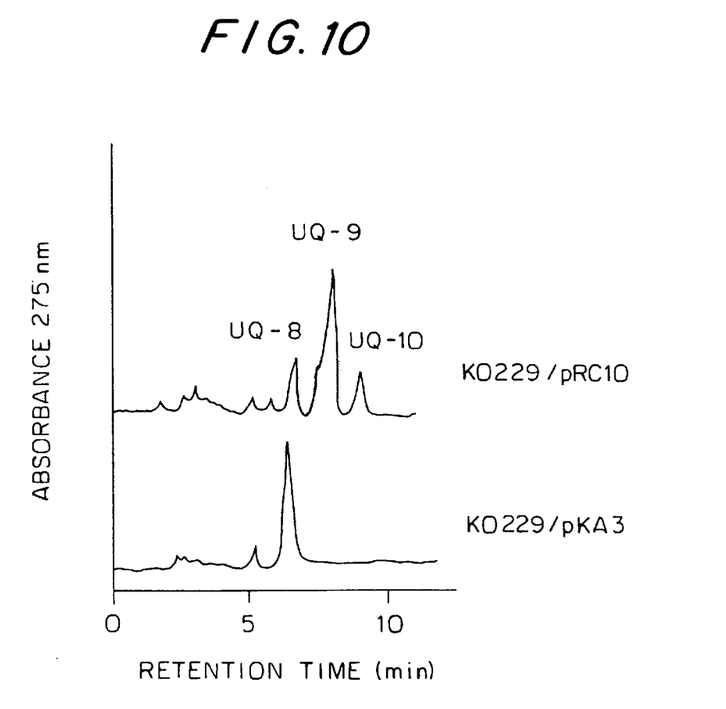
FIG. 10 shows a HPLC chromatogram of UQ extracted from a culture of *E. coli* KO229/pRC10.

In view of its usefulness, the strain whose complementation was thus confirmed was designated *E. coli* KO229/pRC10 and deposited as FERM BP-6062 on Aug. 15, 1997 under the Budapest Treaty with the National Institute of Bioscience and Human-Technology, Agency of Industrial Science and Technology. UQ was extracted in the manner as above from this strain (FERM BP-6062), and the result is shown in FIG. 10. As is evident from this result, formation of UQ-10 was confirmed.

EFFECT OF THE INVENTION

According to the present invention, a structural gene for decaprenyl diphosphate synthase derived from a wide variety of photosynthetic bacteria such as *Rhodobacter capsulatus* was not only successfully isolated and sequenced but could also be expressed in *E. coli* for the first time.

As a result, UQ-10 in addition to UQ-8 and UQ-9 can be made feasible using *E. coli,* and by use of the ispB gene-deficient strain, UQ-10 can be selectively produced in high purity and in a large amount while inhibiting production of UQ-8.

The microorganisms *R. capsulatus, E. coli* DH10B, *E. coli* JM109, *E. coli* KO229 etc. used in the present invention are described in literatures, are commercially available, and are obtainable from Dr. Matuda, Shimane University, Japan.

What is claimed is:

1. An isolated DNA comprising a gene coding for decaprenyl diphosphate synthase (DDS) from *Rhodobacter capsulatus*.

2. The isolated DNA according to claim 1, wherein said gene codes for a decaprenyl diphosphate synthase (DDS) of SEQ ID NO:2.

3. The isolated DNA according to claim 2, wherein said gene coding for DDS, is the dds1 gene comprising the coding sequence of nucleotides 205 to 1182 of SEQ ID NO:1.

4. A plasmid vector comprising the isolated DNA according to claim 1.

5. A plasmid vector, comprising the DNA according to claim 2.

6. Expression plasmid pRC10 comprising the DNA described in claim 2 inserted into vector pUC18.

7. Expression plasmid pRC10 comprising DNA described in claim 3 inserted into vector pUC18.

8. A microorganism transformed with the plasmid vector according to claim 4.

9. The transformed microorganism according to claim 8, which is *Escherichia coli*.

10. A microorganism transformed with a plasmid described in claim 5.

11. A transformed microorganism according to claim 8 wherein the transformed microorganism is *E. coli* DH10B/pRC10 (FERM BP-6061), *E. coli* KO229/pRC10 (FERM BP-6062) or *E. coli* JM109/pRC10.

12. A microorganism transformed with a plasmid described in claim 7.

13. A microorganism transformed with a plasmid described in claim 6.

14. A transformed microorganism according to claim 12 wherein the transformed microorganism is *E. coli* DH10B/pRC10 (FERM BP-6061), *E. coli* KO229/pRC10 (FERM BP-6062) or *E. coli* JM109/pRC10.

15. A transformed microorganism according to claim 7 wherein the transformed microorganism is *E. coli* DH10B/pRC10 (FERM BP-6061), *E. coli* KO229/pRC10 (FERM BP-6062) or *E. coli* JM109/pRC10.

16. A microorganism transformed with a gene coding for decaprenyl diphosphate synthase (DDS) derived from *Rhodobacter capsulatus*.

17. A transformed microorganism according to claim 16 wherein a gene coding for octaprenyl disphophate synthase (OPS) has been destroyed.

18. A method of producing ubiquinone-10, which comprises:
    culturing the transformed microorganism of claim 10 to produce ubiquinone-10; and
    isolating ubiquinone-10 produced by the transformed microorganism.

19. A method of producing ubiquinone-10, which comprises:
    culturing the transformed microorganism of claim 11 to produce ubiquinone-10; and
    isolating ubiquinone-10 produced by the transformed microorganism.

20. A method of producing ubiquinone-10, which comprises:
    culturing the transformed microorganism of claim 13 to produce ubiquinone-10; and
    isolating ubiquinone-10 produced by the transformed microorganism.

21. A method of producing ubiquinone-10, which comprises:
    culturing the transformed microorganism of claim 15 to produce ubiquinone-10; and
    isolating ubiquinone-10 produced by the transformed microorganism.

22. A method of producing ubiquinone-10, which comprises:
    culturing the transformed microorganism of claim 12 to produce ubiquinone-10; and
    isolating ubiquinone-10 produced by the transformed microorganism.

23. A method of producing ubiquinone-10, which comprises:
    culturing the transformed microorganism of claim 14 to produce ubiquinone-10; and
    isolating ubiquinone-10 produced by the transformed microorganism.

24. A method of producing ubiquinone-10, which comprises:
    culturing the transformed microorganism of claim 16 to produce ubiquinone-10; and
    isolating ubiquinone-10 produced by the transformed microorganism.

25. A method of producing ubiquinone-10, which comprises:
    culturing the transformed microorganism of claim 17 to produce ubiquinone-10; and
    isolating ubiquinone-10 produced by the transformed microorganism.

26. A method of producing high-purity ubiquinone-10, which comprises:
    culturing *Escherichia coli* DH10B/pRC10, *Escherichia coli* KO229/prC10 or *Escherichia coli* JM109/pRC10 to produce ubiquinone-10; and
    isolating ubiquinone-10 produced by the transformed microorganism.

* * * * *

SEQUENCE LISTING

```
<160> NUMBER OF SEQ ID NOS: 8

<210> SEQ ID NO 1
<211> LENGTH: 1401
<212> TYPE: DNA
<213> ORGANISM: Rhodobacter capsulatus
<220> FEATURE:
<221> NAME/KEY: CDS
<222> LOCATION: (205)..(1179)

<400> SEQUENCE: 1
```

-continued

```
aagaatatac tcaaaggcag cggaccctaa actaaaggct cccgtctggt ttaagcccta      60
gaattttggc taccttcctg ctgctttag  gatacaatag ctttaatttt ttaagtatca     120
gatatctaaa agctggttac ggtgtttaga cgtctcactg tttaactgtg catccgatta     180
ctttcgcaag aggttctttt tcat atg gcc atc gat ttc aag caa gat att       231
                           Met Ala Ile Asp Phe Lys Gln Asp Ile
                            1               5 ctc gct cct gtt gct caa gat ttt gca gcg atg gac cag ttt att aat       279
Leu Ala Pro Val Ala Gln Asp Phe Ala Ala Met Asp Gln Phe Ile Asn
 10              15                  20                  25 gaa gga atc agc tcc aag gtc gca ctg gtc atg tca gtc agc aag cat       327
Glu Gly Ile Ser Ser Lys Val Ala Leu Val Met Ser Val Ser Lys His
         30                  35                  40 gtc gtt gaa gca ggt gga aag cgc atg cgt ccg att atg tgc ttg ctg       375
Val Val Glu Ala Gly Gly Lys Arg Met Arg Pro Ile Met Cys Leu Leu
             45                  50                  55 gcc gct tat gcc tgt ggt gaa acc aat tta aag cat gca cag aag ctg       423
Ala Ala Tyr Ala Cys Gly Glu Thr Asn Leu Lys His Ala Gln Lys Leu
                 60                  65                  70 gcg gcc att att gaa atg ctg cat acg gcg act ctg gta cat gat gat       471
Ala Ala Ile Ile Glu Met Leu His Thr Ala Thr Leu Val His Asp Asp
 75                  80                  85 gat gta gat gag tct ggc tta cgc cgt ggc aga cca aca gca aat gcg       519
Asp Val Asp Glu Ser Gly Leu Arg Arg Gly Arg Pro Thr Ala Asn Ala
 90                  95                 100                 105 aca tgg aat aac cag act gcg gta ctg gtg ggg gat ttt ctg att gcc       567
Thr Trp Asn Asn Gln Thr Ala Val Leu Val Gly Asp Phe Leu Ile Ala
             110                 115                 120 cgg gca ttt gat ctg ctg gtt gat ctg gac aat atg atc ctg tta aag       615
Arg Ala Phe Asp Leu Leu Val Asp Leu Asp Asn Met Ile Leu Leu Lys
                 125                 130                 135 gac ttc tct aca gga acc tgt gag att gct gag ggt gaa gta ttg cag       663
Asp Phe Ser Thr Gly Thr Cys Glu Ile Ala Glu Gly Glu Val Leu Gln
         140                 145                 150 ttg cag gca cag cat cag cca gat aca aca gaa gat att tat tta cag       711
Leu Gln Ala Gln His Gln Pro Asp Thr Thr Glu Asp Ile Tyr Leu Gln
 155                 160                 165 att att cac ggt aaa acc tca cgg ttg ttc gaa ctg gcg acc gaa ggc       759
Ile Ile His Gly Lys Thr Ser Arg Leu Phe Glu Leu Ala Thr Glu Gly
170                 175                 180                 185 gct gca ata ctg gca ggc aaa cct gaa tac cgt gaa cct tta cgt cgt       807
Ala Ala Ile Leu Ala Gly Lys Pro Glu Tyr Arg Glu Pro Leu Arg Arg
             190                 195                 200 ttt gcc gga cac ttt ggc aat gct ttt cag att att gat gat att ctg       855
Phe Ala Gly His Phe Gly Asn Ala Phe Gln Ile Ile Asp Asp Ile Leu
                 205                 210                 215 gat tac act tca gat gct gat acg ctc ggc aaa aat att ggc gat gac       903
Asp Tyr Thr Ser Asp Ala Asp Thr Leu Gly Lys Asn Ile Gly Asp Asp
         220                 225                 230 ttg atg gaa ggc aaa ccc acc ctg ccg ctg att gca gca atg caa aat       951
Leu Met Glu Gly Lys Pro Thr Leu Pro Leu Ile Ala Ala Met Gln Asn
 235                 240                 245 act caa ggt gaa cag cgc gac ctg atc cgt cgc agc att gcc act ggc       999
Thr Gln Gly Glu Gln Arg Asp Leu Ile Arg Arg Ser Ile Ala Thr Gly
250                 255                 260                 265 ggt act tca cag ctt gaa caa gtt att gcg att gta caa aat tcg gga      1047
Gly Thr Ser Gln Leu Glu Gln Val Ile Ala Ile Val Gln Asn Ser Gly
             270                 275                 280 gcg ctg gat tat tgc cat aag cgt gct act gaa gaa acc gag cga gca      1095
```

```
              Ala Leu Asp Tyr Cys His Lys Arg Ala Thr Glu Glu Thr Glu Arg Ala
                              285                 290                 295 tta cag gca cta gaa ata tta cct gag agt act tac cgg cag gcg ctg            1143
Leu Gln Ala Leu Glu Ile Leu Pro Glu Ser Thr Tyr Arg Gln Ala Leu
                300                 305                 310 gtt aac ttg acc cgc tta gct tta gac cga atc caa taatattatt                 1189
Val Asn Leu Thr Arg Leu Ala Leu Asp Arg Ile Gln
            315                 320             325 aaaaatttta tgcatttaaa ctttcaagat cttttctca gaatgcacca gcagcttgag          1249
caacctcaag ctgtattaga tgaaaatatt cttattgagc tggttaaccg cctacgcccc          1309
gctgatacca aaataccga agaaattgaa agaaaatttc aggcatttat ccagtcgctt           1369
ttaattacac cggctgctgc ctgttacatt tc                                         1401

<210> SEQ ID NO 2
<211> LENGTH: 325
<212> TYPE: PRT
<213> ORGANISM: Rhodobacter capsulatus

<400> SEQUENCE: 2

Met Ala Ile Asp Phe Lys Gln Asp Ile Leu Ala Pro Val Ala Gln Asp
 1               5                  10                  15

Phe Ala Ala Met Asp Gln Phe Ile Asn Glu Gly Ile Ser Ser Lys Val
                20                  25                  30

Ala Leu Val Met Ser Val Ser Lys His Val Val Glu Ala Gly Gly Lys
            35                  40                  45

Arg Met Arg Pro Ile Met Cys Leu Leu Ala Ala Tyr Ala Cys Gly Glu
        50                  55                  60

Thr Asn Leu Lys His Ala Gln Lys Leu Ala Ala Ile Ile Glu Met Leu
 65                 70                  75                  80

His Thr Ala Thr Leu Val His Asp Asp Val Asp Glu Ser Gly Leu
                    85                  90                  95

Arg Arg Gly Arg Pro Thr Ala Asn Ala Thr Trp Asn Asn Gln Thr Ala
                100                 105                 110

Val Leu Val Gly Asp Phe Leu Ile Ala Arg Ala Phe Asp Leu Leu Val
            115                 120                 125

Asp Leu Asp Asn Met Ile Leu Leu Lys Asp Phe Ser Thr Gly Thr Cys
        130                 135                 140

Glu Ile Ala Glu Gly Glu Val Leu Gln Leu Gln Ala Gln His Gln Pro
145                 150                 155                 160

Asp Thr Thr Glu Asp Ile Tyr Leu Gln Ile Ile His Gly Lys Thr Ser
                165                 170                 175

Arg Leu Phe Glu Leu Ala Thr Glu Gly Ala Ala Ile Leu Ala Gly Lys
            180                 185                 190

Pro Glu Tyr Arg Glu Pro Leu Arg Arg Phe Ala Gly His Phe Gly Asn
        195                 200                 205

Ala Phe Gln Ile Ile Asp Asp Ile Leu Asp Tyr Thr Ser Asp Ala Asp
    210                 215                 220

Thr Leu Gly Lys Asn Ile Gly Asp Asp Leu Met Glu Gly Lys Pro Thr
225                 230                 235                 240

Leu Pro Leu Ile Ala Ala Met Gln Asn Thr Gln Gly Glu Gln Arg Asp
                245                 250                 255

Leu Ile Arg Arg Ser Ile Ala Thr Gly Gly Thr Ser Gln Leu Glu Gln
            260                 265                 270

Val Ile Ala Ile Val Gln Asn Ser Gly Ala Leu Asp Tyr Cys His Lys
```

```
                        275                  280                 285
Arg Ala Thr Glu Glu Thr Glu Arg Ala Leu Gln Ala Leu Glu Ile Leu
        290                 295                 300

Pro Glu Ser Thr Tyr Arg Gln Ala Leu Val Asn Leu Thr Arg Leu Ala
305                 310                 315                 320

Leu Asp Arg Ile Gln
                325
```

<210> SEQ ID NO 3
<211> LENGTH: 17
<212> TYPE: DNA
<213> ORGANISM: Rhodobacter capsulatus
<220> FEATURE:
<223> OTHER INFORMATION: Y is T or C; N is A, C, T or G; and R is A or
      G.

<400> SEQUENCE: 3
ytnytncayg aygaygt                                                  17

<210> SEQ ID NO 4
<211> LENGTH: 15
<212> TYPE: DNA
<213> ORGANISM: Rhodobacter capsulatus
<220> FEATURE:
<223> OTHER INFORMATION: Y is T or C; N is A, C, T or G; and R is A or
      G.

<400> SEQUENCE: 4
rtcntcnagy tgrtt                                                    15

<210> SEQ ID NO 5
<211> LENGTH: 26
<212> TYPE: DNA
<213> ORGANISM: Rhodobacter capsulatus

<400> SEQUENCE: 5
cgggatccaa tggccatcga tttcaa                                        26

<210> SEQ ID NO 6
<211> LENGTH: 26
<212> TYPE: DNA
<213> ORGANISM: Rhodobacter capsulatus

<400> SEQUENCE: 6
cccaagcttt tattggattc ggtcta                                        26

<210> SEQ ID NO 7
<211> LENGTH: 21
<212> TYPE: DNA
<213> ORGANISM: Rhodobacter capsulatus

<400> SEQUENCE: 7
aataatctga aaagcattgc c                                             21

<210> SEQ ID NO 8
<211> LENGTH: 21
<212> TYPE: DNA
<213> ORGANISM: Rhodobacter capsulatus

<400> SEQUENCE: 8
tccggcaaaa cgacgtaaag g                                             21